United States Patent
Dieterle et al.

(10) Patent No.: US 6,982,347 B2
(45) Date of Patent: *Jan. 3, 2006

(54) HETEROGENEOUSLY CATALYZED PARTIAL GAS PHASE OXIDATION OF ACROLEIN TO ACRYLIC ACID

(75) Inventors: Martin Dieterle, Mannheim (DE); Jochen Petzoldt, Mannheim (DE); Klaus Joachim Müller-Engel, Stutensee (DE); Heiko Arnold, Nanjing (CN)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/806,460

(22) Filed: Mar. 23, 2004

(65) Prior Publication Data

US 2004/0192963 A1    Sep. 30, 2004

Related U.S. Application Data

(60) Provisional application No. 60/475,794, filed on Jun. 5, 2003.

(30) Foreign Application Priority Data

Mar. 25, 2003  (DE)  ................................ 103 13 211

(51) Int. Cl.
*C07C 51/235*    (2006.01)
(52) U.S. Cl. ................. 562/535; 562/532; 562/531
(58) Field of Classification Search ............. 562/523, 562/531, 532, 533, 534, 535
See application file for complete search history.

(56) References Cited

U.S. PATENT DOCUMENTS

| 6,403,829 | B1 * | 6/2002 | Unverricht et al. ......... 562/532 |
| 6,525,217 | B1 * | 2/2003 | Unverricht et al. ......... 562/544 |
| 6,620,968 | B1 * | 9/2003 | Lonzetta et al. ............ 562/532 |
| 2004/0192963 | A1 | 9/2004 | Dieterle et al. |
| 2004/0192964 | A1 | 9/2004 | Petzoldt et al. |
| 2004/0192965 | A1 | 9/2004 | Petzoldt et al. |
| 2004/0225158 | A1 | 11/2004 | Dieterle et al. |
| 2004/0242926 | A1 | 12/2004 | Dieterle et al. |

FOREIGN PATENT DOCUMENTS

| DE | 199 10 506 | 9/2000 |
| DE | 199 10 508 | 9/2000 |
| DE | 199 27 624 | 12/2000 |
| DE | 199 48 241 | 4/2001 |
| DE | 199 48 248 | 4/2001 |
| DE | 199 48 523 | 4/2001 |
| EP | 1 106 598 | 6/2001 |
| EP | 1 164 120 | 12/2001 |
| WO | WO 01/36364 | 5/2001 |

OTHER PUBLICATIONS

U.S. Appl. No. 10/110,227, filed Apr. 22, 2002, Tenten et al.
U.S. Appl. No. 09/936,184, filed Sep. 10, 2001, Unverricht et al.
U.S. Appl. No. 10/806,460, filed Mar. 23, 2004, Dieterle et al.

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

In a process for partially oxidizing acrolein to acrylic acid in the gas phase under heterogeneous catalysis, the starting reaction gas mixture is oxidized at an acrolein loading of $\leq 145$ and $\geq 70$ l (STP) of acrolein/l of fixed catalyst bed·h over a fixed catalyst bed which is accommodated in two successive reaction zones A, B, the highest temperature of the reaction gas mixture within reaction zone A being above the highest temperature of the reaction gas mixture within reaction zone B.

14 Claims, No Drawings

HETEROGENEOUSLY CATALYZED PARTIAL GAS PHASE OXIDATION OF ACROLEIN TO ACRYLIC ACID

This application is a non-provisional application of provisional application Ser. No. 60/475,794, filed Jun. 5, 2003, which in turn finds basis of priority in German application Serial No. 103 13 211.2 filed Mar. 25, 2003.

BACKGROUND OF THE INVENTION

The present invention relates to a process for partially oxidizing acrolein to acrylic acid in the gas phase under heterogeneous catalysis by conducting a starting reaction gas mixture which comprises acrolein, molecular oxygen and at least one inert gas containing at least 20% by volume of molecular nitrogen and contains the molecular oxygen and the acrolein in a molar $O_2:C_3H_4O$ ratio of $\geq 0.5$ in one reaction stage over a fixed catalyst bed which is arranged in two spatially successive reaction zones A,B, the temperature of reaction zone A being a temperature in the range from 230 to 320° C. and the temperature of reaction zone B likewise being a temperature in the range from 230 to 320° C., whose active composition is at least one multimetal oxide comprising the elements Mo and V, in such a way that reaction zone A extends to an acrolein conversion of from 45 to 85 mol % and, on single pass of the starting reaction gas mixture through the overall fixed catalyst bed, the acrolein conversion is $\geq 90$ mol % and the selectivity of acrylic acid formation, based on acrolein converted, is $\geq 90$ mol %, the chronological sequence in which the starting reaction gas mixture flows through the reaction zones corresponding to the alphabetic sequence of the reaction zones.

DESCRIPTION OF THE BACKGROUND

The abovementioned process for catalytically oxidizing acrolein to acrylic acid in the gas phase is generally known (cf., for example, DE-A 19910508) and is especially significant as the second oxidation stage in the preparation of acrylic acid by two-stage catalytic gas phase oxidation starting from propene. Acrylic acid is an important monomer which finds use as such or in the form of its alkyl ester for obtaining polymers suitable, for example, as adhesives.

In addition to molecular oxygen and the reactants, the starting reaction gas mixture contains inert gas in order to keep the reaction gas outside the explosion range, among other reasons.

One objective of such a heterogeneously catalyzed partial gas phase oxidation of acrolein to acrylic acid is to achieve a very high yield $Y^{AA}$ of acrylic acid (this is the number of moles of acrolein converted to acrylic acid, based on the number of moles of acrolein used) on single pass of the reaction gas mixture through the reaction stage under otherwise predefined boundary conditions.

A further objective of such a heterogeneously catalyzed partial gas phase oxidation of acrolein to acrylic acid is to achieve a very high space-time yield ($STY^{AA}$) of acrylic acid (in a continuous procedure, this is the total amount of acrylic acid obtained per hour and per liter of volume of the fixed catalyst bed used).

At a constant given yield $Y^{AA}$, the greater the hourly space velocity of acrolein from the fixed catalyst bed of the reaction stage (this refers to the amount of acrolein in liters (STP)=l (STP); the volume in liters which would be taken up by the appropriate amount of acrolein under standard conditions, i.e. at 25° C. and 1 bar) which is conducted as a constituent of the starting reaction gas mixture per hour through one liter of fixed catalyst bed).

The teachings of the documents WO 01/36364, DE-A 19927624, DE-A 19948248, DE-A 19948523, DE-A 19948241 and DE-A 19910506 are therefore directed toward significantly increasing the hourly space velocity of acrolein on the fixed catalyst bed of the reaction stage at substantially constant $Y^{AA}$. This is achieved substantially by arranging the fixed catalyst bed in the reaction stage in two spatially successive temperature zones (reaction zones). The hourly space velocity of acrolein on the fixed catalyst bed is selected at $\geq 150$ l (STP)/l of fixed catalyst bed·h and the temperature of the second (in the flow direction of the reaction gas mixture) temperature zone has to be at least 10° C. above the temperature of the first temperature zone.

In a similar manner, EP-A 1106598 also teaches a process of the high loading method for the heterogeneously catalyzed partial gas phase oxidation of acrolein to acrylic acid, in which the fixed catalyst bed of the reaction stage is arranged in a plurality of temperature zones. According to a teaching of EP-A 1106598, the temperature difference of a subsequent temperature zone in the flow direction of the reaction gas mixture can be either more or less than 5° C. above the temperature of the preceding temperature zone, and EP-A 1106598 leaves completely open the question of under which conditions a larger and under which conditions a smaller temperature difference should be used.

EP-A 1106598 also leaves completely open the definition of the temperature of a reaction zone or a temperature zone.

In contrast, the remaining prior art documents define the temperature of a reaction zone as the temperature of the fixed catalyst bed disposed in the reaction zone when performing the process in the absence of a chemical reaction. When this temperature is not constant within the reaction zone, the term temperature of a reaction zone refers to the (numerical) mean of the temperature of the fixed catalyst bed along the reaction zone. It is essential that the individual reaction zones are heated substantially independently of one another, so that one reaction zone always corresponds to one temperature zone. The above definition of the temperature of a reaction zone also applies in this document.

Since the heterogeneously catalyzed partial gas phase oxidation of acrolein to acrylic acid is a markedly exothermic reaction, the temperature of the reaction gas mixture on reactive pass through the fixed catalyst bed is generally different to the temperature of a reaction zone. It is normally above the temperature of the reaction zone and generally proceeds within a reaction zone through a maximum (heating point maximum) or falls starting from a maximum value.

However, a disadvantage of the teachings of the prior art is that they are directed exclusively toward operating a multizone arrangement under a higher acrolein loading. This is disadvantageous in that such a procedure is inevitably accompanied by a high $STY^{AA}$. However, this requires an appropriate market demand for acrylic acid. When the latter is absent (for example temporarily), the multizone arrangement necessarily has to be operated at lower acrolein loadings, and a target parameter to be pursued which then comes to the forefront is a very high selectivity of acrylic acid formation, based on acrolein converted ($S^{AA}$). This is the molar amount of acrylic acid formed in single pass through the multizone arrangement, based on the number of moles of acrolein converted.

SUMMARY OF THE INVENTION

It is an object of the present invention to provide a process for heterogeneously catalyzed partial gas phase oxidation of acrolein to acrylic acid in a multizone arrangement, in which acrylic acid is formed with very high selectivity at acrolein loadings of <150 l (STP)/l·h.

We have found that this object is achieved by a process for partially oxidizing acrolein to acrylic acid in the gas phase under heterogeneous catalysis by conducting a starting reaction gas mixture which comprises acrolein, molecular oxygen and at least one inert gas containing at least 20% by volume of molecular nitrogen and contains the molecular oxygen and the acrolein in a molar $O_2:C_3H_4O$ ratio of $\geq 0.5$ in one reaction stage over a fixed catalyst bed which is arranged in two spatially successive reaction zones A,B, the temperature of reaction zone A being a temperature in the range from 230 to 320° C. and the temperature of reaction zone B likewise being a temperature in the range from 230 to 320° C., whose active composition is at least one multimetal oxide comprising the elements Mo and V, in such a way that reaction zone A extends to an acrolein conversion of from 45 to 85 mol % and, on single pass of the starting reaction gas mixture through the overall fixed catalyst bed, the acrolein conversion is $\geq 90$ mol % and the selectivity of acrylic acid formation, based on acrolein converted, is $\geq 90$ mol %, the chronological sequence in which the starting reaction gas mixture flows through the reaction zones corresponding to the alphabetic sequence of the reaction zones, wherein a) the hourly space velocity of the acrolein contained in the starting reaction gas mixture on the fixed catalyst bed is $\leq 145$ l (STP) of acrolein/l of fixed catalyst bed·h and $\geq 70$ l (STP) of acrolein/l of fixed catalyst bed·h, b) the volume-specific activity of the fixed catalyst bed is either constant or increases at least once in the flow direction of the reaction gas mixture over the fixed catalyst bed, and c) the difference $T^{maxA}-T^{maxB}$, formed from the highest temperature $T^{maxA}$ which the reaction gas mixture has within the reaction zone A and the highest temperature $T^{maxB}$ which the reaction gas mixture has within reaction zone B, is $\geq 0°$ C.

DETAILED DESCRIPTION OF THE PREFERRED EMBODIMENTS

Advantageously, the volume-specific activity of the fixed catalyst bed increases at least once in the flow direction.

In general, the difference $T^{maxA}-T^{maxB}$ in the process according to the invention will not be more than 75° C. According to the invention, $T^{maxA}-T^{maxB}$ is preferably $\geq 3°$ C. and $\leq 60°$ C. Very particular preference is given to $T^{maxA}-T^{maxB}$ in the process according to the invention being $\geq 5°$ C. and $\leq 40°$ C.

The process according to the invention proves advantageous, for example, when the hourly space velocity of the acrolein contained in the starting reaction gas mixture on the fixed catalyst bed is $\geq 70$ l (STP) of acrolein/l·h and $\leq 140$ l (STP) of acrolein/l·h, or $\geq 70$ l (STP) of acrolein/l·h and $\leq 135$ l (STP) of acrolein/l·h or $\geq 70$ l (STP) of acrolein/l·h and $\leq 140$ l (STP) of acrolein/l·h, or $\geq 80$ l (STP) of acrolein/l·h and $\leq 130$ l (STP) of acrolein/l·h, or $\geq 90$ l (STP) of acrolein/l·h, and $\leq 125$ l (STP) of acrolein/l·h, or $\geq 100$ l (STP) of acrolein/l·h and $\leq 120$ l (STP) of acrolein/l·h, or $\geq 105$ l (STP) of acrolein/l·h and $\leq 115$ l (STP) of acrolein/l·h.

It will be appreciated that the process according to the invention can also be applied when the hourly space velocity of acrolein contained in the reaction gas mixture on the fixed catalyst bed is <70 l (STP) of acrolein/l·h and/or the volume-specific activity of the fixed catalyst bed is constant. However, the operation of a multizone arrangement at such low reactant loadings would hardly be economic.

When performing the process according to the invention, the differences $T^{maxA}-T^{maxB}$ required in accordance with the invention are normally attained when, on the one hand, both the temperature of reaction zone A and the temperature of reaction zone B are in the range from 230 to 320° C. and, on the other hand, the difference between the temperature of reaction zone B ($T_B$) and the temperature of reaction zone A ($T_A$), i.e. $T_B-T_A$, is $\leq 0°$ C. and $\geq -10°$ C., or $\leq 0°$ C. and $\geq -5°$ C., or frequently $\leq 0°$ C. and $\geq -3°$ C.

In other word, in contrast to the teaching of the prior art for high loadings, the temperature of the subsequent zone in the process according to the invention will normally be lower than the temperature of the preceding reaction zone.

The above statement relating to the temperature differences $T_B-T_A$ also applies when the temperature of reaction zone A is in the preferred range of from 250 to 300° C. or in the preferred range of from 260 to 280° C.

The working pressure in the process according to the invention can either be below atmospheric pressure (for example down to 0.5 bar) or above atmospheric pressure. Typically, the working pressure will be at values of from 1 to 5 bar, frequently from 1 to 3 bar. Normally, the reaction pressure will not exceed 100 bar.

According to the invention, preference is given to reaction zone A extending to an acrolein conversion of from 50 to 85 mol % or from 60 to 85 mol %.

In general, the acrolein conversion based on single pass in the process according to the invention can be $\geq 92$ mol %, or $\geq 94$ mol %, or $\geq 96$ mol %, or $\geq 98$ mol % and frequently even $\geq 99$ mol %. The selectivity of acrylic acid formation will generally be $\geq 92$ mol %, or $\geq 94$ mol %, frequently $\geq 95$ mol % or $\geq 96$ mol % or $\geq 97$ mol %.

According to the invention, the molar $O_2$:acrolein ratio in the starting reaction gas mixture has to be $\geq 0.5$. It is frequently at values of $\geq 1$. Typically, this ratio will be at values of $\leq 3$. According to the invention, the molar $O_2$:acrolein ratio in the starting reaction gas mixture will be from 1 to 2 or from 1 to 1.5.

Useful catalysts for the fixed catalyst bed of the catalytic gas phase oxidation of acrolein according to the invention are all of those whose active composition is at least one multimetal oxide comprising Mo and V. Such suitable multimetal oxide catalysts can be taken, for example, from U.S. Pat. No. 3,775,474, U.S. Pat. No. 3,954,855, U.S. Pat. No. 3,893,951 and U.S. Pat. No. 4,339,355. Also particularly suitable are the multimetal oxide compositions of EP-A 427508, DE-A 2909671, DE-C 3151805, DE-B 2626887, DE-A 4302991, EP-A 700893, EP-A 714700 and DE-A 19736105 and also DE-A 10046928.

Also suitable in this context are the exemplary embodiments of EP-A 714700 and also of DE-A 19736105.

A multiplicity of the multimetal oxide active compositions suitable for the fixed catalyst bed, for example those of DE-A 19815281, can be encompassed by the general formula IV

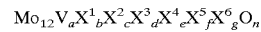  (IV)

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=0 from 0 to 40 and
n=a number which is determined by the valency and frequency of the elements in IV other than oxygen.

Embodiments among the active multimetal oxides IV which are preferred according to the invention are those which are encompassed by the following definitions of the variables of the general formula IV:
$X^1$=W, Nb, and/or Cr,
$X^2$=Cu, Ni, Co, and/or Fe,
$X^3$=Sb,
$X^4$=Na and/or K,
$X^5$=Ca, Sr and/or Ba,
$X^6$=Si, Al, and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in IV other than oxygen.

However, multimetal oxides IV which are very particularly preferred according to the invention are those of the general formula V

$$Mo_{12}V_{a'}Y^1_{b'}Y^2_{c'}Y^5_{f'}Y^6_{g'}O_{n'} \qquad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in V other than oxygen.

The multimetal oxide compositions (IV) which are suitable according to the invention are obtainable in a manner known per se, for example disclosed in DE-A 4335973 or in EP-A 714700.

In principle, multimetal oxide active compositions, in particular those of the general formula IV, suitable for the catalysts of the fixed catalyst bed can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically reduces with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to effecting the intimate mixing in wet form.

This is typically done by mixing the starting compounds in the form of an aqueous solution and/or suspension. Particularly intimate dry mixtures are obtained in the mixing processes described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, in particular those of the general formula IV, are generally used in the fixed catalyst bed not in powder form, but rather shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is advantageous. It will be appreciated that the supported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2909671, EP-A 293859 or from EP-A 714700.

To coat the support bodies, the powder composition to be applied is advantageously moistened and is dried again after application, for example by means of hot air. The layer thickness of the powder composition applied to the support body is advantageously selected within the range from 10 to 1 000 µm, preferably within the range from 50 to 500 µm and more preferably in the range from 150 to 250 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders having a grit layer. It is suitable to use substantially nonporous, surface-roughened, spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Advantageous multimetal oxide active compositions to be used for the catalysts of the fixed catalyst bed are also compositions of the general formula VI $$[D]_p[E]_q \quad (VI)$$

where the variables are defined as follows:
$D = Mo_{12}V_{a''}Z^1_{b''}Z^2_{c''}Z^3_{d''}Z^4_{e''}Z^5_{f''}Z^6_{g''}O_{x''}$,
$E = Z^7_{12}Cu_{h''}H_{i''}O_{y''}$,
$Z^1$ = W, Nb, Ta, Cr and/or Ce,
$Z^2$ = Cu, Ni, Co, Fe, Mn and/or Zn,
$Z^3$ = Sb and/or Bi,
$Z^4$ = Li, Na, K, Rb, Cs and/or H
$Z^5$ = Mg, Ca, Sr and/or Ba,
$Z^6$ = Si, Al, Ti and/or Zr,
$Z^7$ = Mo, W, V, Nb and/or Ta, preferably Mo and/or W
$a''$ = from 1 to 8,
$b''$ = from 0.2 to 5,
$c''$ = from 0 to 23,
$d''$ = from 0 to 50,
$e''$ = from 0 to 2,
$f''$ = from 0 to 5,
$g''$ = from 0 to 50,
$h''$ = from 4 to 30,
$i''$ = from 0 to 20 and
$x'', y''$ = numbers which are determined by the valency and frequency of the elements in VI other than oxygen and
$p, q$ = numbers other than zero whose p/q ratio is from 160:1 to 1:1, and which are obtainable by separately preforming a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo^{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition at temperatures of from 250 to 600° C. to give the desired catalyst geometry before or after drying.

Preference is given to the multimetal oxide compositions VI in which the preformed solid starting composition 1 is incorporated into an aqueous starting composition 2 at a temperature of <70° C. A detailed description of the preparation of multimetal oxide VI catalysts is contained, for example, in EP-A 668104, DE-A 19736105, DE-A 10046928, DE-A 19740493 and DE-A 19528646.

With regard to the shaping, the statements made for the multimetal oxide IV catalysts apply to the multimetal oxide VI catalysts.

Further suitable multimetal oxide compositions for the catalysts of the fixed catalyst bed are those of DE-A 19815281, in particular all exemplary embodiments from this document. With regard to the shaping, the same applies as was stated above.

For the fixed catalyst bed of the process according to the invention, particularly suitable catalysts are the coated catalysts S1 (stoichiometry: $Mo_{12}V_3W_{1.2}Cu_{2.4}O_n$) and S7 (stoichiometry: $Mo_{12}V_3W_{1.2}Cu_{1.6}Ni_{0.8}O_n$) from DE-A 4442346 having an active composition fraction of 27% by weight and a coating thickness of 230 µm, the coated catalyst from preparative example 5 of DE-A 10046928 (stoichiometry: $Mo_{12}V_3W_{1.2}Cu_{2.4}O_n$) having an active composition fraction of 20% by weight, the coated catalysts of examples 1 to 5 from DE-A 19815281, but equally the abovementioned coated catalysts for the second reaction stage applied to support rings of geometry 7 mm×3 mm×4 mm (external diameter×length×internal diameter) having an active composition fraction of 20% by weight (based on the overall composition of the coated catalyst), and also a coated catalyst having a biphasic active composition of stoichiometry $(Mo_{10.4}V_3W_{1.2}O_x)$ $(CuMo_{0.5}W_{0.5}O_4)_{1.6}$ and prepared according to DE-A 19736105 and having an active composition fraction of 20% by weight applied to the abovementioned 7 mm×3 mm×4 mm support.

The catalysts recommended above for the reaction stage according to the invention are only suitable for the reaction stage according to the invention when everything is retained except the support geometry which is changed to 5 mm×3 mm×1.5 mm (external diameter×length×internal diameter). The multimetal oxides mentioned can also be used in the reaction stage according to the invention in the form of the corresponding unsupported catalyst rings.

To prepare the fixed catalyst bed in the process according to the invention, it is possible to use only the shaped catalyst bodies having the appropriate multimetal oxide active composition or else substantially homogeneous mixtures of shaped catalyst bodies having multimetal oxide active composition and shaped bodies (shaped diluent bodies) behaving substantially inertly with regard to the heterogeneously catalyzed partial gas phase oxidation and having no multimetal oxide active composition. Useful materials for such inert shaped bodies include in principle all of those which are also suitable as support material for coated catalysts suitable according to the invention. Useful such materials include, for example, porous or nonporous aluminum oxide, silicon dioxide, thorium dioxide, zirconium dioxide, silicon carbide, silicates such as magnesium silicate or aluminum silicate or the steatite already mentioned above (e.g. Steatit C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted by them.

According to the invention, it is advantageous when the chemical composition of the active composition used does not vary over the fixed catalyst bed. In other words, although the active composition used for a single shaped catalyst body can be a mixture of different multimetal oxides comprising the elements Mo and V, the same mixture then has to be used for all shaped catalyst bodies of the fixed catalyst bed.

In this case, the volume-specific (i.e. normalized to the unit of volume) activity can be reduced in a simple manner, for example, by homogeneously diluting a basic amount of shaped catalyst bodies prepared in a uniform manner with shaped diluent bodies. The higher the proportion of shaped diluent bodies selected, the less the active composition and catalyst activity contained in a certain volume of the bed.

A volume-specific activity increasing at least once in the flow direction of the reaction gas mixture over the fixed catalyst bed can therefore be attained for the process according to the invention in a simple manner, for example, by beginning the bed with a high proportion of inert shaped diluent bodies based on one type of shaped catalyst bodies, and then either continuously or, at least once or more than once, abruptly (for example stepwise) reducing this proportion of shaped diluent bodies in the flow direction. However, an increase in the volume-specific activity is also possible, for example, by increasing the thickness of the active composition layer applied to the support at a constant geometry and active composition type of a coated shaped catalyst body, or, in a mixture of coated catalysts having the same geometry but having different proportions by weight of the active composition, increasing the proportion of shaped catalyst bodies having higher active composition contents. Alternatively, the active compositions themselves can be diluted in the course of the active composition preparation by, for example, incorporating inert, diluting materials such as hard-fired silica into the dry mixture of the starting compounds to be calcined. Different amounts of diluting material added lead automatically to different activities. The more diluting material is added, the lower the resulting activity will be. A similar effect can also be achieved, for example, in mixtures of unsupported catalysts and of coated catalysts (having identical active composition) by varying the mixing ratio in an appropriate manner. It will be appreciated that the variants described can also be used in combination.

It is of course also possible to use mixtures of catalysts having chemically different active compositions and, as a consequence of these different compositions, having different activities for the fixed catalyst bed. These mixtures may in turn be diluted in inert diluent bodies.

Normally, the volume-specific activity will decrease not once within the fixed catalyst bed in the flow direction of the reaction gas mixture in the process according to the invention.

Upstream and/or downstream of the fixed catalyst bed may be disposed beds consisting exclusively of inert material (for example only fixed diluent bodies) (in this document, they are not included for terminology purposes in the fixed catalyst bed, since they contain no shaped bodies which have multimetal oxide active composition). The shaped diluent bodies used for the inert bed can have the same geometry as the shaped catalyst bodies used in the fixed catalyst bed. However, the geometry of the shaped diluent bodies used for the inert bed can also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4–5 mm.

According to the invention, the fixed catalyst bed in the process according to the invention is preferably structured as follows in the flow direction of the reaction gas mixture:

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed bed catalyst bed, a homogeneous mixture or two (having decreasing dilution) successive homogeneous mixtures of shaped catalyst bodies and shaped diluent bodies (both preferably having substantially the same geometry), in which the proportion by weight of shaped diluent bodies (the mass densities of shaped catalyst bodies and of shaped diluent bodies generally differing only slightly) is normally from 10 to 50% by weight, preferably from 20 to 45% by weight and more preferably from 25 to 35% by weight. According to the invention, this first zone is then advantageously followed to the end of the length of the fixed catalyst bed (i.e., for example, to a length of from 2.00 to 3.00 m, preferably from 2.50 to 3.00 m) by either a bed of the shaped catalyst bodies diluted only to a slighter extent (than in the first zone) or, most preferably, an unaccompanied bed of the same shaped catalyst bodies which have also been used in the first zone.

The aforementioned applies in particular when the shaped catalyst bodies used in the fixed catalyst bed are coated catalyst rings or coated catalyst spheres (in particular those which are listed in this document as preferred). For the purposes of the aforementioned structuring, both the shaped catalyst bodies or their support rings and the shaped diluent bodies in the process according to the invention substantially have the ring geometry 7 mm×3 mm×4 mm (external diameter×length×internal diameter).

The abovementioned also applies when, instead of inert shaped diluent bodies, shaped coated catalyst bodies are used whose active composition content is from 2 to 15% by weight lower than the active composition content of the shaped coated catalyst bodies at the end of the fixed catalyst bed 2.

In an advantageous manner from an application point of view, the reaction stage of the process according to the invention is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the reaction stage of the process according to the invention.

In other words, in the simplest manner, the fixed catalyst bed to be used in accordance with the invention (possibly with downstream and/or upstream inert beds) is disposed in the metal tubes of a tube bundle reactor and two spatially separated heating media, generally salt melts, are conducted, around the metal tubes. The tube section over which the particular salt bath extends represents a reaction zone in accordance with the invention.

In other words, in the simplest manner, for example, a salt bath A flows around that section of the tubes (reaction zone A) in which acrolein is oxidatively converted (on single pass) until a conversion value in the range from 45 to 85 mol %, (preferably from 50 to 85 mol %, more preferably from 60 to 85 mol %) is achieved and a salt bath B flows around the section of the tube (reaction zone B) in which the acrolein is subsequently oxidatively converted (on single pass) until a conversion value of at least 90 mol % is achieved (if required, the reaction zones A,B to be used in accordance with the invention can be followed by further reaction zones which are maintained at individual temperatures).

It is advantageous from an application point of view if the reaction stage of the process according to the invention includes no further reaction zones. In other words, the salt bath B advantageously flows around the sections of the tubes in which acrolein is subsequently oxidatively converted (on single pass) up to a conversion value of $\geq 92$ mol %, or $\geq 94$ mol % or $\geq 96$ mol % or $\geq 98$ mol % and frequently even $\geq 99$ mol % or more.

Typically, the beginning of the reaction zone B lies beyond the heating point maximum of reaction zone A.

According to the invention, both salt baths A, B can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in reaction zone A and countercurrent flow in reaction zone B (or vice versa).

In all of the aforementioned cases, it will be appreciated that a transverse flow can be superimposed on the parallel flow of the salt melts relative to the reaction tubes taking place within the particular reaction zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Typically, the catalyst tubes for the reaction stage according to the invention in the aforementioned two-zone tube bundle reactors are manufactured from ferritic steel and typically have a wall thickness of from 1 to 3 mm. Their internal diameter is generally from 20 to 30 mm, frequently from 22 to 26 mm. Their length is advantageously from 3 to 4 m, preferably 3.5 m. In each temperature zone, the fixed catalyst bed occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the distance between the central internal axes of immediately adjacent catalyst tubes (the catalyst tube pitch) is from 35 to 45 mm (cf., for example, EP-B 468290).

Useful heat exchange media are in particular fluid heating media. It is particularly advantageous to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors of the reaction stage according to the invention, the flow rate within the two heat exchange medium circuits required is selected in such a way that the temperature of the heat exchange medium rises from the entrance into the reaction zone to the exit from the reaction zone by from 0 to 15° C. In other words, the aforementioned $\Delta T$ may be from 1 to 10° C., or from 2 to 8° C., or from 3 to 6° C., in accordance with the invention.

According to the invention, the entrance temperature of the heat exchange medium into reaction zone A is normally in the range from 230 to 320° C., preferably in the range from 250 to 300° C. and more preferably in the range from 260 to 280° C. According to the invention, the entrance temperature of the heat exchange medium into reaction zone B is likewise in the range from 230 to 280° C., but at the same time normally, in accordance with the invention, from $\geq 0°$ C. to $\leq 10°$ C., or $\geq 0°$ C. and $\leq 5°$ C., or frequently $\geq 0°$ C. and $\leq 3°$ C., below the entrance temperature of the heat exchange medium entering reaction zone A.

It is pointed out once again at this juncture that, for an implementation of the reaction stage of the process according to the invention, it is possible to use in particular the two-zone tube bundle reactor type described in DE-B 2201528 which includes the possibility of removing a portion of the hotter heat exchange medium of reaction zone B to reaction zone A, in order to optionally heat a cold starting reaction gas mixture or a cold cycle gas. The tube bundle characteristics within an individual reaction zone may also be configured as described in EP-A 382 098.

The process according to the invention normally uses acrolein which has been obtained by catalytic gas phase oxidation of propene. In general, the acrolein-containing reaction gases of this propene oxidation are used without intermediate purification, which is why the starting reaction gas mixture according to the invention can also contain small amounts of, for example, unconverted propene or of by-products of propene oxidation. Normally, the oxygen required for the acrolein oxidation also has to be added to the product gas mixture of the propene oxidation.

Advantageously, such a catalytic oxidation of the propene to acrolein in the gas phase preceding the process according to the invention is carried out in a similar manner to the process according to the invention, in such a way that a starting reaction gas mixture which comprises propene, molecular oxygen and at least one inert gas, and contains the molecular oxygen and the propene in a molar $O_2:C_3H_6$ ratio of $\geq 1$ is conducted in one reaction stage over a fixed catalyst bed which is arranged in two spatially successive reaction zones A', B', the temperature of reaction zone A' being a temperature in the range from 290 to 380° C. and the temperature of reaction zone B' likewise being a temperature in the range from 290 to 380° C., and this active composition is at least one multimetal oxide comprising the elements Mo, Fe and Bi, in such a way that the reaction zone A' extends to a conversion of the propene of from 40 to 80 mol % and the propene conversion on single pass through the fixed catalyst bed 1 is $\geq 90$ mol % and the accompanying selectivity of acrolein formation and also of acrylic acid by-production taken together is $\geq 90$ mol %, wherein a) the hourly space velocity on the fixed catalyst bed of the propene contained in the starting reaction gas mixture is $\leq 160$ l (STP) of propene/l of fixed catalyst bed 1·h and $\geq 90$ l (STP) of propene/l of fixed catalyst bed 1·h;

b) the volume-specific activity of the fixed catalyst bed in the flow direction of the reaction gas mixture over the fixed catalyst bed is either constant or increases at least once, and c) the difference $T^{maxA'}-T^{maxB'}$, formed from the highest temperature $T^{maxA'}$ which the reaction gas mixture has within reaction zone A' and the highest temperature $T^{maxB'}$ which the reaction gas mixture has within reaction zone B', is $\geq 0°$ C.

In general, the difference $T^{maxA'}-T^{maxB'}$ will not be more than 80° C. Preferably, $T^{maxA'}-T^{maxB'}$ is $\geq 3°$ C. and $\leq 70°$ C. Most preferably, $T^{maxA'}-T^{maxB'}$ is $\geq 20°$ C. and $\leq 60°$ C.

It proved to be advantageous when the hourly space velocity on the fixed catalyst bed of the propene contained in the starting reaction gas mixture is ≧90 l (STP) of propene/l·h and ≦155 l (STP) of propene/l·h, or ≧100 l (STP) of propene/l·h and ≦150 l (STP) of propene/l·h, or ≧110 l (STP) of propene/l·h and ≦145 l (STP) of propene/l·h, or ≧120 l (STP) of propene/l·h and ≦140 l (STP) of propene/l·h or ≧125 l (STP) of propene/l·h and ≦135 l (STP) of propene/l·h.

When performing the process, the differences $T^{maxA'} - T^{maxB'}$ required are normally attained when, on the one hand, both the temperature of reaction zone A' and the temperature of reaction zone B' are in the range from 290 to 380° C. and, on the other hand, the difference between the temperature of reaction zone B' ($T_{B'}$) and the temperature of reaction zone A' ($T_{A'}$), i.e. $T_{B'} - T_{A'}$, is ≦0° C. and ≧-10° C., or ≦0° C. and ≧-5° C., or frequently ≦0° C. and ≧-3° C.

In other words, when carrying out the process according to the invention, two two-zone tube bundle reactors can be connected in series or combined to a four-zone tube bundle reactor, as described, for example, in WO 01/36364, and the propene oxidation can be carried out in the first two-zone portion and the acrolein oxidation according to the invention in the second two-zone portion.

In the second case, an inner bed is normally disposed between the fixed catalyst beds for the two reaction stages. However, such an intermediate inert bed can also be dispensed with.

Of course, the propene oxidation stage can also be a one-zone tube bundle reactor which is separate or combined in an appropriate manner with the subsequent acrolein oxidation stage.

In the case of combination, the length of the reaction tubes in many cases corresponds to the sum of the lengths of the uncombined tube bundle reactors.

The propene content in the starting reaction gas mixture for the reaction stage preceding the process according to the invention may, for example, be at values of from 4 to 15% by volume, frequently from 5 to 12% by volume, or from 5 to 8% by volume (based in each case on the total volume).

Frequently, the process preceding the process according to the invention will be carried out at a propene:oxygen:inert gases (including steam) volume ratio in the starting reaction gas mixture of 1:(1.0 to 3.0):(5 to 25), preferably 1:(1.4 to 2.3):(10 to 15). In general, at least 20% of the volume of the inert gas will consist of molecular nitrogen. However, it may also consist of ≧30% by volume, or ≧40% by volume, or ≧50% by volume, or ≧60% by volume, or ≧70% by volume, or ≧80% by volume, or ≧90% by volume, or ≧95% by volume, of molecular nitrogen (in this document, inert diluent gases are generally those of which less than 5%, preferably less than 2%, is converted on single pass through the particular reaction stage; in addition to molecular nitrogen, these are, for example, gases such as propane, ethane, methane, pentane, butane, $CO_2$, CO, steam and/or noble gases). Of course, the inert diluent gas in the process preceding the process according to the invention may also consist of up to 50 mol %, or up to 75 mol % and more, of propane. Another constituent of the diluent gas may also be cycle gas, as remains after the removal of the acrylic acid from the product gas mixture of the process according to the invention.

Useful catalysts for such a catalyst propene oxidation in the gas phase are in particular those of EP-A 15565, EP-A 575897, DE-A 19746210 and DE-A 19855913.

The acrolein content in the starting reaction gas mixture for the process according to the invention may, for example, be at values of from 3 to 15% by volume, frequently from 4 to 10% by volume or from 5 to 8% by volume (based in each case on the total volume).

Frequently, the process according to the invention will be carried out at an acrolein: oxygen:steam:inert gas volume ratio (I(STP)) present in the starting reaction gas mixture of 1:(1 to 3):(0 to 20):(3 to 30), preferably of 1:(1 to 3):(0.5 to 10):(7 to 10).

However, it will be appreciated that the process according to the invention can also be performed at an acrolein: oxygen:steam:others volume ratio (I(STP)) present in the starting reaction gas mixture of 1:(0.9 to 1.3):(2.5 to 3.5):(10 to 12).

It is emphasized at this point that the multimetal oxide compositions of DE-A 10261186 are also advantageous as active compositions for the fixed catalyst bed of the process according to the invention.

Embodiments which are advantageous according to the invention of a two-zone tube bundle reactor for a propene partial oxidation stage preceding the reaction stage according to the invention can have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst Tubes:
material of the catalyst tubes: ferritic steel;
dimensions of the catalyst tubes: length, for example, 3 500 mm;
external diameter, for example, 30 mm;
wall thickness, for example, 2 mm;
number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter, for example, 8 mm and wall thickness of, for example, 1 mm;
reactor (same material as the catalyst tubes):
cylindrical vessel of internal diameter 6 000–8 000 mm;
reactor hoods plated with stainless steel of the type 1.4541; plating thickness: a few mm;
annularly arranged tube bundle, for example with free central space:
diameter of the free central space: for example, 1 000–2 500 mm (for example 1 200 mm, or 1 400 mm, or 1 600 mm, or 1 800 mm, or 2 000 mm, or 2 200 mm, or 2 400 mm);
normally homogeneous catalyst tube distribution in the tube bundle (6 equidistant adjacent tubes per catalyst tube), arrangement in an equilateral triangle, catalyst tube pitch (separation of the central internal axes of immediately adjacent catalyst tubes): 35–45 mm, for example 36 mm, or 38 mm, or 40 mm, or 42 mm, or 44 mm;
the catalyst tubes are secured and sealed by their ends in catalyst tube plates (upper plates and lower plates each having a thickness, for example, of 100–200 mm) and open at their upper ends into a hood joined to the vessel which has an inlet for the starting reaction gas mixture; a separating plate of thickness 20–100 mm disposed, for example, at half the catalyst tube length, divides the reactor space symmetrically into two reaction zones (temperature zones) A' (upper zone) and B' (lower zone); each reaction zone is divided into 2 equidistant longitudinal sections by deflecting plates;

the deflecting plate preferably has annular geometry; the catalyst tubes are advantageously secured and sealed at the separating plate; they are not secured and sealed at the deflecting plates, so that the transverse flow rate of the salt melts within one zone is very constant;

each zone is provided with salt melt as a heat carrier by its own salt pump; the feed of the salt melt is, for example, below the deflecting plate and the withdrawal is, for example, above the deflecting plate;

a substream is, for example, removed from both salt melt circuits and cooled, for example, in one column or two separate indirect heat exchangers (steam generation);

in the first case, the cooled salt melt stream is divided, combined with the particular residual stream and pressurized by the particular pump into the appropriate annular channel which divides the salt melt over the circumference of the vessel; the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence from the outside inward,
from the inside outward;

the salt melt flows through a window mounted around the circumference of the vessel and collects at the end of each zone in an annular channel disposed around the reactor jacket, in order to be pumped in a circuit including substream cooling;

the salt melt is conducted from bottom to top through each reaction zone.

The reaction gas mixture leaves the reactor of the reaction stage according to the invention at a temperature a few degrees higher than the salt bath entrance temperature of the first reactor. For further processing, the reaction gas mixture is advantageously cooled in a separate aftercooler which is connected downstream of this reactor to from 220° C. to 280° C., preferably from 240° C. to 260° C.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.

Salt Melt:

The salt melt used may be a mixture of 53% by weight of potassium nitrate, 40% by weight of sodium nitrite and 7% by weight of sodium nitrate; both reaction zones and the aftercooler advantageously use a salt melt of the same composition; the amount of salt pumped by circulation in the reaction zones may be approx. 10 000 m³/h per zone.

Flow Control:

The starting reaction gas mixture advantageously flows from top to bottom through the reactor, while the salt melts having different temperatures of the individual zones are advantageously conveyed from bottom to top;

Catalyst tube and thermal tube charge (from top to bottom), for example:

Section 1: length 50 cm
steatite rings of geometry 7 mm×7 mm×4 mm (external diameter×length×internal diameter) as a preliminary bed.

Section 2: length 140 cm
catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm
catalyst charge of annular (5 mm×3 mm×2 mm=external diameter×length×internal diameter) unsupported catalyst according to example 1 of DE-A 10046957 (stoichiometry: $[Bi_2W_2O_9 \times 2 WO_3]_{0.5}$ $[Mo_{12}Co_{5.5}Fe_{2.94}Si_{1.59}K_{0.08}O_x]_1$).

Configurations of a two-zone tube bundle reactor for the acrolein reaction stage according to the invention which are advantageous in accordance with the invention can be designed as follows:

Everything as in the two-zone tube bundle reactor for the propene reaction stage. However, the thickness of the upper and lower catalyst tube plate is frequently 100–200 mm, for example 110 mm, or 130 mm, or 150 mm, or 170 mm, or 190 mm.

The aftercooler is dispensed with; instead, the lower openings of the catalyst tubes open into a hood which is connected to the container at the lower end and has an outlet for the product gas mixture; the upper reaction zone is zone A and the lower reaction zone is zone B. Between the outlet "aftercooler" and the inlet "reactor for the reaction stage according to the invention" is advantageously a means for feeding compressed air.

The catalyst tube and thermal tube charge (from top to bottom) can, for example, be as follows:

Section 1: length 20 cm
steatite rings of geometry 7 mm×7 mm×4 mm (external diameter×length×internal diameter) as a preliminary bed.

Section 2: length 90 cm
catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm
catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm
catalyst charge of annular (7 mm×3 mm×4 mm external diameter×length×internal diameter) coated catalyst according to preparative example 5 of DE A 10046928 (stoichiometry: $Mo_{12}V_3W_{1.2}Cu_{2.4}O_x$).

Alternatively, the propene stage catalyst tube and thermal tube charge (from bottom to top) can also have the following appearance:

Section 1: length 50 cm
steatite rings of geometry 7 mm×7 mm×4 mm (external diameter×length×internal diameter) as a preliminary bed.

Section 2: length 300 cm
catalyst charge of annular (5 mm×3 mm×2 mm=external diameter×length×internal diameter) unsupported catalyst according to example 1 of DE-A 10046957 (stoichiometry: $[Bi_2W_2O_9 \times 2WO_3]_{0.5}$· $[Mo_{12}Co_{5.6}Fe_{2.94}Si_{1.59}K_{0.08}O_x]_1$).

The acrolein stage catalyst tube and thermal tube charge can also have the following appearance (from top to bottom):

Section 1: length 20 cm
steatite rings of geometry 7 mm×7 mm×4 mm (external diameter×length×internal diameter) as a preliminary bed.

Section 2: length 140 cm
  catalyst charge of a homogeneous mixture of 25% by weight of steatite rings of geometry 7 mm×3 mm×4 mm (external diameter×length×internal diameter) and 75% by weight of coated catalyst from section 3.
Section 3: length 190 cm
  catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

In all of the propene charges mentioned, the unsupported catalyst from example 1 of DE-A 10046957 can also be replaced by:
a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \cdot 10\ SiO_2$;
b) example No. 3 of DE-A 19855913 as an unsupported hollow cylinder catalyst of geometry 5 mm×3 mm×2 mm or 5 mm×2 mm×2 mm;
c) unsupported multimetal oxide II catalyst according to example 1 of DE-A 19746210;
d) one of the coated catalysts 1, 2 and 3 of DE-A 10063162, except applied in the same coating thickness to support rings of geometry 5 mm×3 mm×1.5 mm, or 7 mm×3 mm×1.5 mm.
e) a coated catalyst according to the implementation examples of DE-A 19815281, except applied in the same coating thickness to support rings of geometry 7 mm×3 mm×4 mm, or 8 mm×6 mm×4 mm (always external diameter×length×internal diameter).

In the above list, the support material used is preferably steatite from CeramTec (C220).

In all the abovementioned acrolein stage charges according to the invention, the coated catalyst can be replaced in accordance with preparative example 5 of DE-A 10046928:
a) coated catalyst S1 or S7 from DE-A 4442346 having an active composition content of 27% by weight and a coating thickness of 230 µm;
b) a coated catalyst according to examples 1 to 5 of DE 19815281, except applied to support rings of geometry 7 mm×3 mm×4 mm having an active composition content of 20% by weight;
c) coated catalyst having biphasic active composition of stoichiometry $(Mo_{10.4}V_3W_{1.2}O_x)\ (CuMo_{0.5}W_{0.5}O_4)_{1.6}$, prepared according to DE-A 19736105 and having an active composition content of 20% by weight, applied to the abovementioned 7 mm×3 mm×4 mm support.

According to the invention, the fixed catalyst bed for the propene oxidation stage and the fixed catalyst bed for the acrolein oxidation stage according to the invention are advantageously otherwise selected in such a way (for example by dilution with, for example, inert material) that the temperature difference between the heating point maximum of the reaction gas mixture in the individual reaction zones and the particular temperature of the reaction zone generally does not exceed 80° C. This temperature difference is usually ≦70° C., frequently from 20 to 70° C., and this temperature difference is preferably small. For safety reasons, these fixed catalyst beds are also selected in a manner known per se to those skilled in the art (for example by dilution with, for example, inert material) in such a way that the peak-to-salt-temperature sensitivity as defined in EP-A 1106598 is ≦9° C., or ≦7° C., or ≦5° C., or ≦3° C.

Aftercooler and reactor for the acrolein reaction stage are connected by a connecting tube whose length is less than 25 m.

The reactor arrangement described and all other reactor arrangements and charges with fixed bed catalyst described in this document can also be operated at high propene and acrolein loadings, as described in the documents WO 01/36364, DE-A 19927624, DE-A 19948248, DE-A 19948523, DE-A 19948241, DE-A 19910506, DE-A 10302715 and EP-A 1106598.

The reaction zones A', B'; or A, B can preferably have the temperatures recommended in this document, although in such a way that the second reaction zone in each case, in accordance with the teaching of the abovementioned documents, has a higher temperature than the first reaction zone in each case. The heating point temperature in the second reaction zone in each case is preferably always below that of the first reaction zone in each case.

However, the acrolein loadings according to the invention in the procedure according to the invention result in an increased selectivity of acrylic acid formation relative to the procedure recommended for high acrolein loadings.

In the examples and comparative examples which follow and also in the reactor arrangement below, the annular shaped diluent bodies and the annular shaped catalyst bodies in the acrolein reaction stage can also be replaced by spherical shaped diluent bodies and spherical shaped catalyst bodies (each having radius from 2 to 5 mm and having an active composition content of from 10 to 30% by weight, frequently from 10 to 20% by weight). The statement relating to operation at high acrolein loadings in the above documents retains its validity.

EXAMPLES AND COMPARATIVE EXAMPLES

A reaction tube (V2A steel; external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) was charged from top to bottom as follows:

Section 1: length 20 cm
  steatite rings of geometry 7 mm×7 mm×4 mm (external diameter×length×internal diameter) as a preliminary bed.
Section 2: length 90 cm
  catalyst charge of a homogeneous mixture of 30% by weight of steatite rings of geometry 7 mm×3 mm×4 mm (external diameter×length×internal diameter) and 70% by weight of coated catalyst from section 4.
Section 3: length 50 cm
  catalyst charge of a homogeneous mixture of 20% by weight of steatite rings of geometry 7 mm×3 mm×4 mm (external diameter×length×internal diameter) and 80% by weight of coated catalyst from section 4.
Section 4: length 190 cm
  catalyst charge of annular (7 mm×3 mm×4 mm external diameter×length×internal diameter) coated catalyst according to preparative example 5 of DE A 10046928 (stoichiometry: $Mo_{12}V_3W_{1.2}Cu_{2.4}O_x$).

The first 175 cm from top to bottom were thermostatted by means of a salt bath A pumped in countercurrent. The second 175 cm were thermostatted by means of a salt bath B pumped in countercurrent.

Gas Phase Oxidation:

The above-described first reaction stage was continuously charged with a starting reaction gas mixture of the following composition, and the loading and the thermostatting of the reaction tube were varied:

5.5% by volume of acrolein,
0.3% by volume of propene,
6.0% by volume of molecular oxygen,
0.4% by volume of CO,
0.8% by volume of $CO_2$,
9.0% by volume of water, and
78.0% by volume of nitrogen.

The reaction gas mixture flowed through a reaction tube from top to bottom.

The pressure at the entrance to the reaction tube varied between 1.6 and 2.1 bar as a function of the acrolein hourly space velocity.

A small sample was taken from the product gas mixture at the reaction tube exit for gas chromatography analysis. At the end of reaction zone A, there was likewise an analysis point.

The results achieved as a function of the selected hourly space velocities and the selected salt bath temperatures are shown by the following table (the letter E in brackets means example and the letter C in brackets means comparative example).

$T_A$, $T_B$, are the temperatures of the salt baths circulated by pumping in the reaction zones A and B.

$C_{AA}$ is the acrolein conversion at the end of reaction zone A in mol %.

$C_{AB}$ is the acrolein conversion at the end of reaction zone B in mol %.

$S^{AA}$ is the selectivity of acrylic acid formation in the product gas mixture, based on converted acrolein, in mol %.

$T^{maxA}$, $T^{maxB}$ are the highest temperature of the reaction gas mixture within reaction zones A and B in °C.

TABLE

| Acrolein hourly space velocity (l(STP)/l·h) | $T_A$ | $T_B$ | $T^{maxA}$ | $T^{maxB}$ | $C_{AA}$ | $C_{AB}$ | $S^{AA}$ |
|---|---|---|---|---|---|---|---|
| 106 (E) | 260 | 260 | 302 | 276 | 80.7 | 99.3 | 95.4 |
| 108 (E) | 262 | 259 | 312 | 275 | 84.8 | 99.3 | 95.8 |
| 104 (C) | 257 | 262 | 285 | 291 | 64.0 | 99.3 | 94.9 |
| 152 (C) | 263 | 269 | 303 | 287 | 78.8 | 99.3 | 95.8 |
| 147 (C) | 257 | 278 | 278 | 310 | 61.3 | 99.3 | 95.0 |

We claim:

1. A process for partially oxidizing acrolein to acrylic acid in the gas phase under heterogeneous catalysis, comprising: passing a starting gas mixture which comprises acrolein, molecular oxygen and at least one inert gas containing at least 20% by volume of molecular nitrogen and contains molecular oxygen and the acrolein in a molar $O_2:C_3H_4O$ ratio of $\geq 0.5$ through one reaction stage over a fixed catalyst bed which is arranged in two spatially successive reaction zones A,B, the temperature of reaction zone A being a temperature in the range from 230 to 320° C. and the temperature of reaction zone B likewise being a temperature in the range from 230 to 320° C., whose active composition in each reaction zone is at least one multimetal oxide comprising the elements Mo and V, in such a way that reaction zone A extends to an acrolein conversion ranging from 45 to 85 mol % and, on single pass of the starting gas mixture through the fixed catalyst bed, the acrolein conversion is $\geq 90$ mol % and the selectivity to acrylic acid, based on acrolein converted is $\geq 90$ mol %, the chronological sequence in which the starting gas mixture flows through the reaction zones corresponding to the alphabetic sequence of the reaction zones, wherein a) the hourly space velocity of the acrolein contained in the starting gas mixture over the fixed catalyst bed is $\leq 145$ l (STP) of acrolein/l of fixed catalyst bed·h and $\geq 70$ l (STP) of acrolein/l of fixed catalyst bed·h, b) the volume-specific activity of the fixed catalyst bed is either constant or increases at least once in the flow direction of the reaction gas mixture over the fixed catalyst bed, and c) the difference $T^{maxA}-T^{maxB}$, determined from the highest temperature $T^{maxA}$ which the reaction gas mixture has within the reaction zone A and the highest temperature $T^{maxB}$ which the reaction gas mixture has within reaction zone B, is $\geq 0°$ C.

2. The process as claimed in claim 1, wherein the difference $T^{maxA}-T^{maxB}$ is $\geq 0°$ C. and $\leq 75°$ C.

3. The process as claimed in claim 1, wherein the difference $T^{maxA}-T^{maxB}$ is $\geq 3°$ C. and $\leq 60°$ C.

4. The process as claimed in claim 1, wherein the difference $T^{maxA}-T^{maxB}$ is $\geq 5°$ C. and $\leq 40°$ C.

5. The process as claimed in claim 1, wherein the hourly space velocity of the acrolein contained in the starting gas mixture over the fixed catalyst bed is $\geq 70$ l (STP) of acrolein/l·h and $\leq 140$ l (STP) of acrolein/l·h.

6. The process as claimed in claim 1, wherein the hourly space velocity of the acrolein contained in the starting gas mixture on the fixed catalyst bed is $\geq 80$ l (STP) of acrolein/l·h and $\leq 130$ l (STP) of acrolein/l·h.

7. A process as claimed in claim 1, wherein the active composition of the fixed catalyst bed is at least one multimetal oxide active composition of the formula IV

$$Mo_{12}V_aX^1_bX^2_cX^3_dX^4_eX^5_fX^6_gO_n \qquad (IV)$$

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40, and
n=a number which is determined by the valency and frequency of the elements other than oxygen in IV.

8. The process as claimed in claim 1, wherein the volume-specific activity of the fixed catalyst bed increases at least once in the flow direction of the reaction gas mixture over the fixed catalyst bed.

9. The process as claimed in claim 1, wherein the difference between the temperature of the reaction zone B ($T_B$) and the temperature of the reaction zone A ($T_A$) is $\leq 0°$ C. to $\geq -10°$ C.

10. The process as claimed in claim 9, wherein the difference between the temperature of the reaction zone B ($T_B$) and the temperature of the reaction zone A ($T_A$) is $\leq 0°$ C. to $\geq -5°$ C.

11. The process as claimed in claim 10, wherein the difference between the temperature of the reaction zone B ($T_B$) and the temperature of the reaction zone A ($T_A$) is $\leq 0°$ C. to $\geq -3°$ C.

12. The process as claimed in claim 10, wherein the pressure within the reaction zones ranges from 1 to 5 bar.

13. The process as claimed in claim 10, wherein the conversion of acrolein in reaction zone A ranges from 50 to 85 mol %.

14. The process as claimed in claim 10, wherein the conversion of acrolein in reaction zone A ranges from 60 to 85 mol %.

* * * * *